(12) United States Patent
Syud et al.

(10) Patent No.: US 8,318,456 B2
(45) Date of Patent: Nov. 27, 2012

(54) TWO HELIX BINDERS

(75) Inventors: Faisal Ahmed Syud, Clifton Park, NY (US); Jack Mathew Webster, Albany, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 13/479,009

(22) Filed: May 23, 2012

(65) Prior Publication Data

US 2012/0253006 A1   Oct. 4, 2012

Related U.S. Application Data

(63) Continuation of application No. 11/608,590, filed on Dec. 8, 2006, now Pat. No. 8,198,043.

(51) Int. Cl.
*C07K 14/435* (2006.01)
*C07H 21/02* (2006.01)
*C12P 21/06* (2006.01)

(52) U.S. Cl. ............... 435/69.1; 435/325; 435/320.1; 530/324; 536/23.1

(58) Field of Classification Search ................ None
See application file for complete search history.

(56) References Cited

U.S. PATENT DOCUMENTS

| | | | |
|---|---|---|---|
| 5,143,844 | A | 9/1992 | Abrahmsen et al. |
| 5,831,012 | A | 11/1998 | Nilsson et al. |
| 6,013,763 | A | 1/2000 | Braisted et al. |
| 6,197,927 | B1 | 3/2001 | Braisted et al. |
| 6,534,628 | B1 | 3/2003 | Nilsson et al. |
| 6,548,639 | B1 | 4/2003 | Frykberg et al. |
| 6,602,977 | B1 | 8/2003 | Ljungqvist et al. |
| 6,740,734 | B1 | 5/2004 | Nilsson et al. |

FOREIGN PATENT DOCUMENTS

WO   WO2005003156   1/2005

OTHER PUBLICATIONS

Braisted, A.C. and James A. Wells, "Minimizing a binding domain from protein A", Proc. Natl. Acad. Sci. USA. vol. 93, pp. 5688-5692, Jun. 1996.

Nedwidek, M.N. and Michael H. Hecht, "Minimized protein structures: A little goes a long way", Proc. Natl. Acad. Sci. USA. vol. 94, pp. 10010-10011, Sep. 1997.

Starovasnik, M. A., et al., "Structural mimicry of a native protein by a minimized binding domain", Proc. Natl. Acad. Sci. USA. vol. 94, pp. 10080-10085, Sep. 1997.

Gunneriusson, E., K. Nord, et al., "Affinity Maturation of a Taq DNA Polymerase Specific Affibody by Helix Shuffling", Protein Eng vol. 12, No. 10, 1999, pp. 873-878.

Wahlberg, E., C. Lendel, et al., "An Affibody in Complex with a Target Protein: Structure and Coupled Folding", Proc. Natl. Acad. Sci. USA. vol. 100, No. 6, Mar. 18, 2003, pp. 3185-3190.

Hogbom, et al., Proc. Natl. Acad. Sci. USA. vol. 100, (6), 3191-3196 (2003).

Hey, Thomas, Erik Fielder, et al., "Artificial, Non-antibody Binding Proteins for Pharmaceutical and Industrial Applications", Trends in Biotechnology, vol. 23, No. 10, Oct. 2005, pp. 514-522.

Engfeldt, T., B Renbert, et al., "Chemical Synthesis of Triple-Labelled Three-Helix Bundle Binding Proteins for Specific Fluorescent Detection of Unlabelled Protein", Chembiochem vol. 6, No. 6, 2005, pp. 1043-1050.

Orlova, Anna, et al., "Tumor Imaging Using a Picomolar Affinity HER2 Binding Affibody Molecule", Cancer Res 2006; 66: (8). Apr. 15, 2006, pp. 4339-4348.

Tolmachev, V., et al., "IN-Benzyl-DTPA-ZHER2:342, an Affibody-Based Conjugate for In Vivo Imaging of HER2 Expression in Malignant Tumors", J of Nuclear Medicine, vol. 47, No. 5, May 2006, pp. 846-853.

PCT/US2007/086708 Search Report—Jul. 21, 2008.

*Primary Examiner* — Kagnew H Gebreyesus
(74) *Attorney, Agent, or Firm* — Fletcher Yoder, P.C.

(57) ABSTRACT

Provided herein are isolated polypeptides derived from the *staphylococcal* protein A protein B domain comprising a pair of anti-parallel alpha helices that are capable of binding a target. Also provided are nucleic acid sequences encoding such two helix binders, vectors containing the nucleic acid sequences encoding for two helix binders, and host cells transformed with vectors containing the nucleic acid sequences encoding for the two-helix binders. Also provided are methods of using the two helix binders.

11 Claims, 9 Drawing Sheets

TWO HELIX BINDERS

CROSS-REFERENCE TO RELATED APPLICATION

Figure 1:
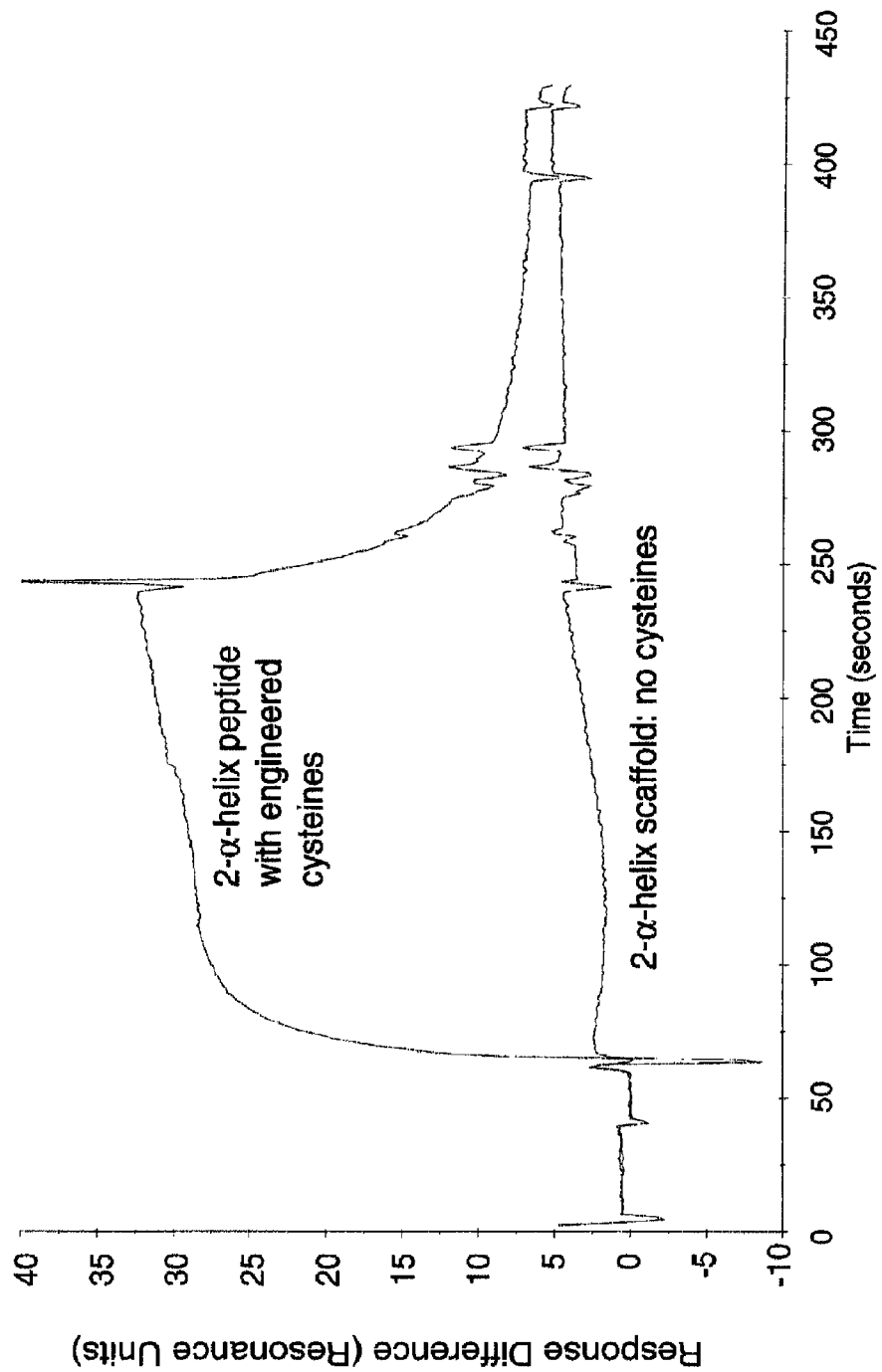

This application is a continuation of application Ser. No. 11/608,590, filed Dec. 8, 2006, entitled "TWO HELIX BINDERS" in the name of Faisal Ahmed Syud et al. and assigned to General Electric Company, which is incorporated by reference herein in its entirety.

The instant application contains a Sequence Listing which has been submitted in ASCII format via EFS-Web and is hereby incorporated by reference in its entirety. Said ASCII copy, created on May 18, 2012, is named 215536-1.txt and is 6,066 bytes in size.

FIELD

The field of invention relates to polypeptides that form multiple helices and are capable of binding to a target.

BACKGROUND

Naturally occurring *Staphylococcal* protein A forms a three-helix structure that bind to the Fc region of IgG. The Z domain of the 58-residue polypeptide derived from the B domain of staphylococcal protein A retains binding.

Affibodies, derived from the Z-domain of protein A, contain a scaffold that are three α-helices connected by loops, where all three helices are required for binding to any other molecule, and 13 amino acids are mutated in the helical segment to provide diversity of binding against targets. Sequence and binding data on a number of affibodies document that 13 sites on these helices can tolerate mutation to any amino acid and maintain binding activity to a target.

BRIEF DESCRIPTION

Provided herein are polypeptide sequences of the staphylococcal protein A, Z binding domain that exclude the third helix, fold into a pair of helices, and demonstrate the ability to bind target. The present invention provides isolated polypeptides comprising a two helix segment derived from the Z domain of protein A stabilized with a disulfide bond between two members of a thiol-containing pair of residues, wherein at least one member of the disulfide pair is positioned outside of the binding interface of the polypeptide.

In some embodiments, the sequence consists of SEQ ID NO.:2, and conservative variants thereof; wherein $X_2$ is any naturally occurring amino acid or analog thereof. In some embodiments employing SEQ ID NO.:2 neither member of the disulfide pair is located at position 5, 6, 7, 9, 10, 13, 14, 20, 21, 23, 24, 28, or 31.

In other embodiments, isolated polypeptide is comprised of the sequence of SEQ ID NO.:3 and conservative variants thereof, wherein $X_1$ is either Glu or Asp.

In other embodiments, the sequence may consist of SEQ ID NO.:5, SEQ ID NO.:6, SEQ ID NO.:7, or conservative variants thereof. In yet other embodiments, the sequence may consist of SEQ ID NO.:8, SEQ ID NO.:9, SEQ ID NO.:10, or conservative variants thereof.

Also provide herein are vectors comprising the nucleic acid of the invention, host cells (e.g., a eukaryotic cell, a prokaryotic cell, and a plant cell) transformed with the vectors.

FIGURES

These and other features, aspects, and advantages of the present invention will become better understood when the following detailed description is read with reference to the accompanying figures.

FIG. 1 depicts the relative binding analysis of crude peptide with and without engineered cysteines. Approximately 5 μg/ml of crude product from each peptide synthesis was analyzed for binding to Her2 using surface plasmon resonance (Biacore). Little to no detectable binding was observed for the two-alpha-helix peptide with no cysteines. However, the peptide with engineered cysteines shows significant binding to Her2. No attempt was made to control disulfide formation for this experiment. The binding observed is most likely a result of spontaneous disulfide formation through the engineered cysteines.

Figure 2:
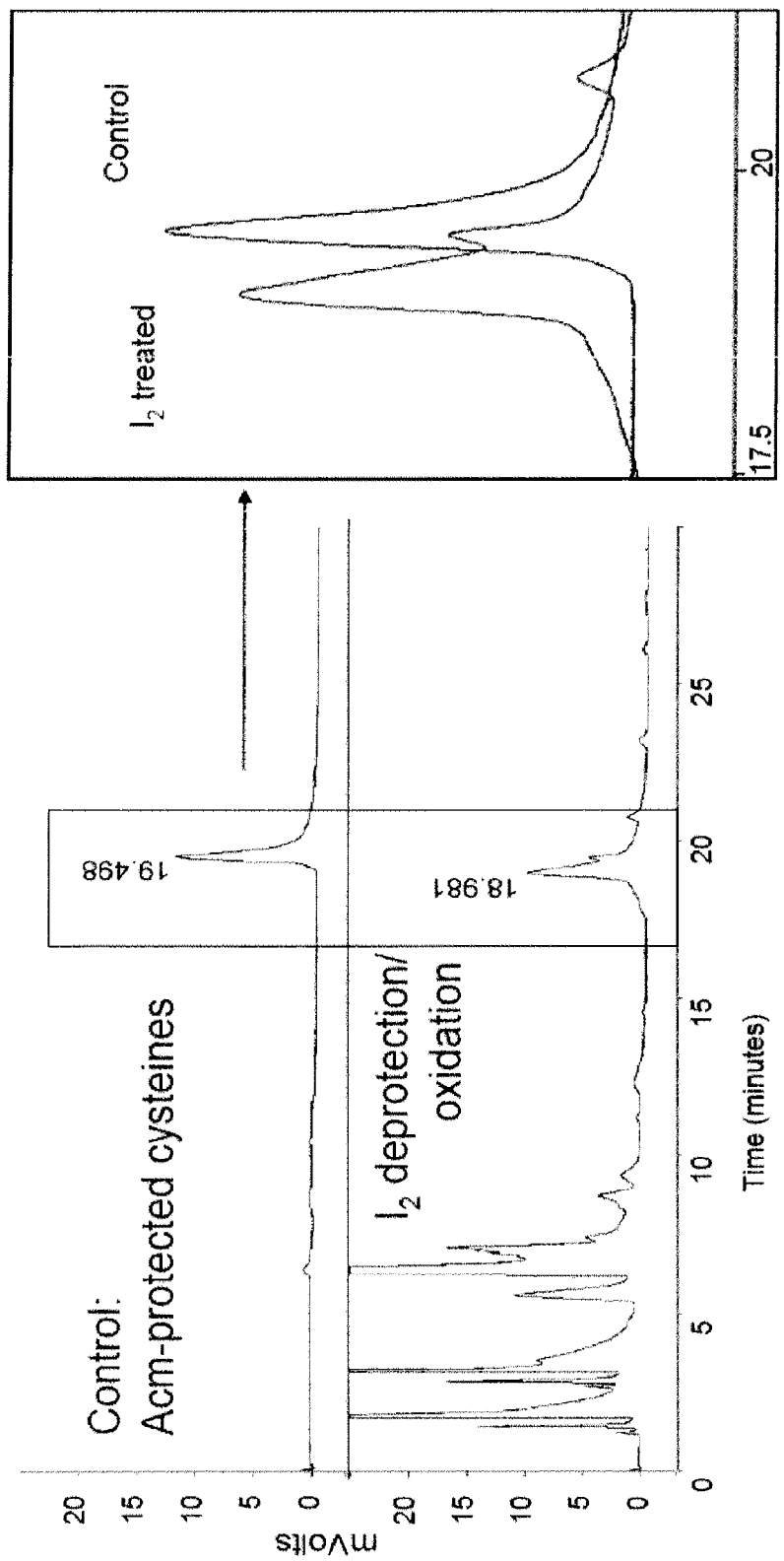

FIG. 2 depicts RP-HPLC analysis of purified anti-Her2 two helix peptide (SEQ. ID. NO.:8) with Acm-protected cysteines compared to the Iodine deprotected-oxidized anti-Her2 two-alpha helix peptide with a disulfide bond. Two peptides compared using the same RP-HPLC conditions. Control Acm-protected anti-Her2 two-alpha-helix peptide has a retention time of 19.49 minutes. The iodine treated peptide has a shift in retention time to 18.98 minutes. This change is a reflection of the loss of two Acm-protecting groups and formation of an intramolecular disulfide bond. Fractions corresponding to these two peaks were collected for analysis by mass spectrometry and surface plasmon resonance, and confirmed to be the claimed products.

Figure 3:
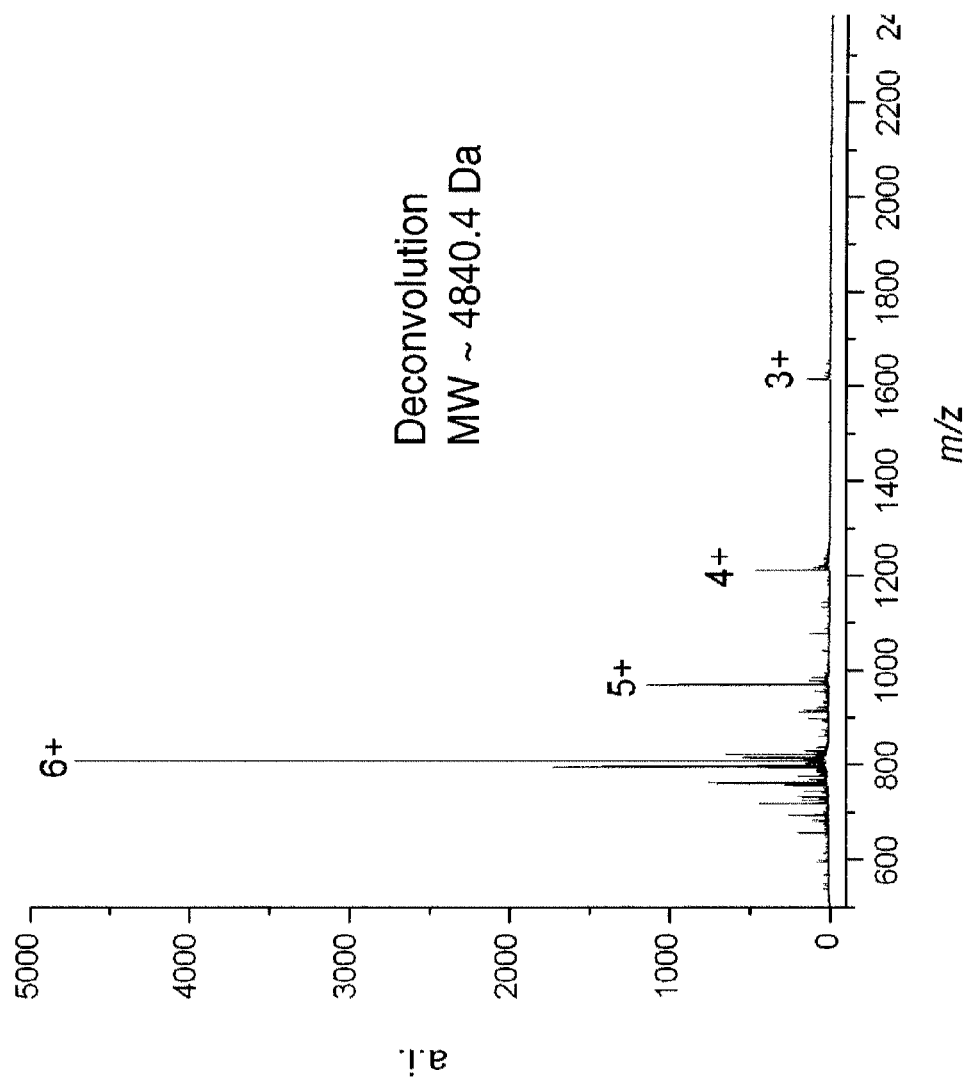

FIG. 3 depicts ESI-MS analysis of the control peptide: Acm-protected cysteines. Collected fractions corresponding to the control Acm-protected peptide (shown in FIG. 4 with a retention time of 19.498) were analyzed by ESI-MS. The formula weight is as predicted for the desired peptide with two Acetamidomethyl groups protecting the cysteine side chain. Peptide+2(Acm)[4698.4+2(71)]=4840.4 daltons.

Figure 4:
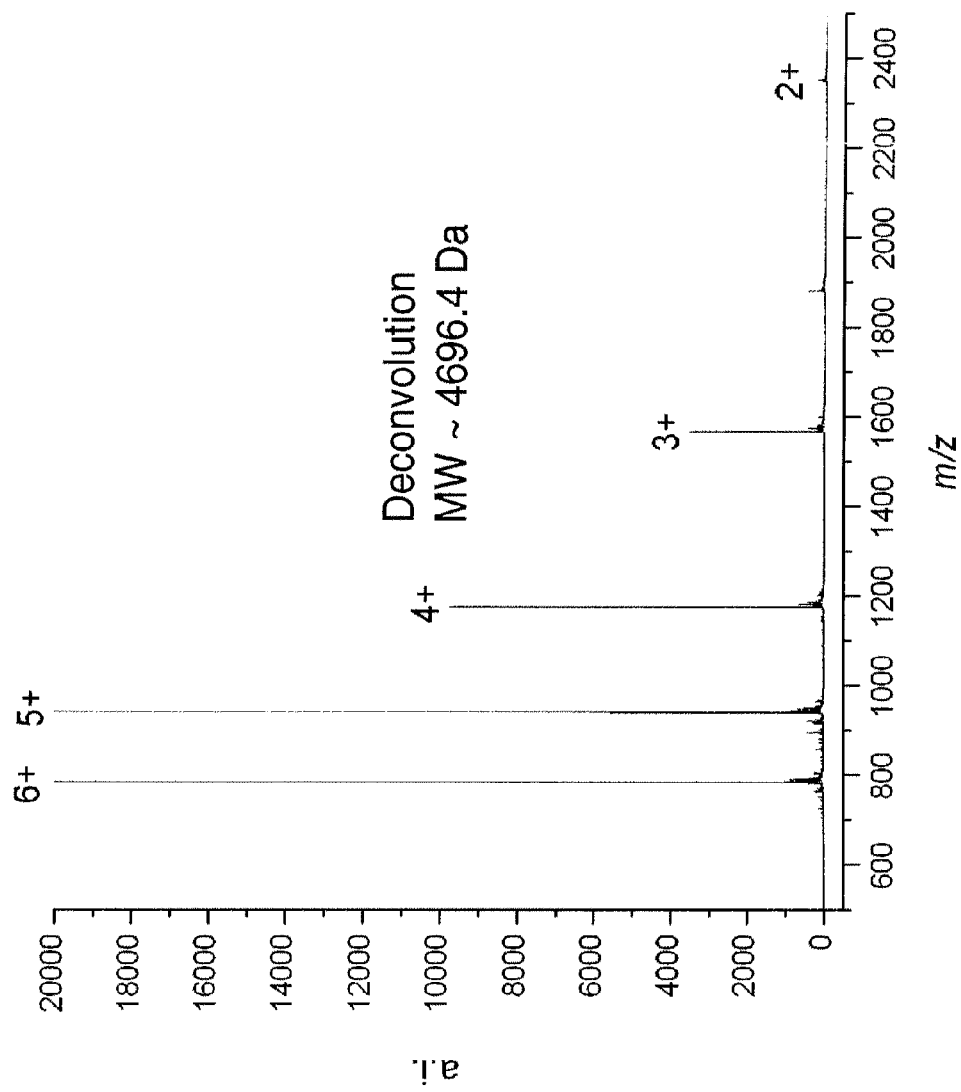

FIG. 4 depicts ESI-MS analysis of the anti-Her2 two helix peptide. Collected fractions corresponding to the $I_2$ deprotected/oxidized peptide shown in FIG. 4 with a retention time of 18.98. The formula weight is as predicted for the desired peptide with one disulfide bridge. Peptide+disulfide bond [4698.4−2(H)]=4696.4 daltons.

Figure 5:
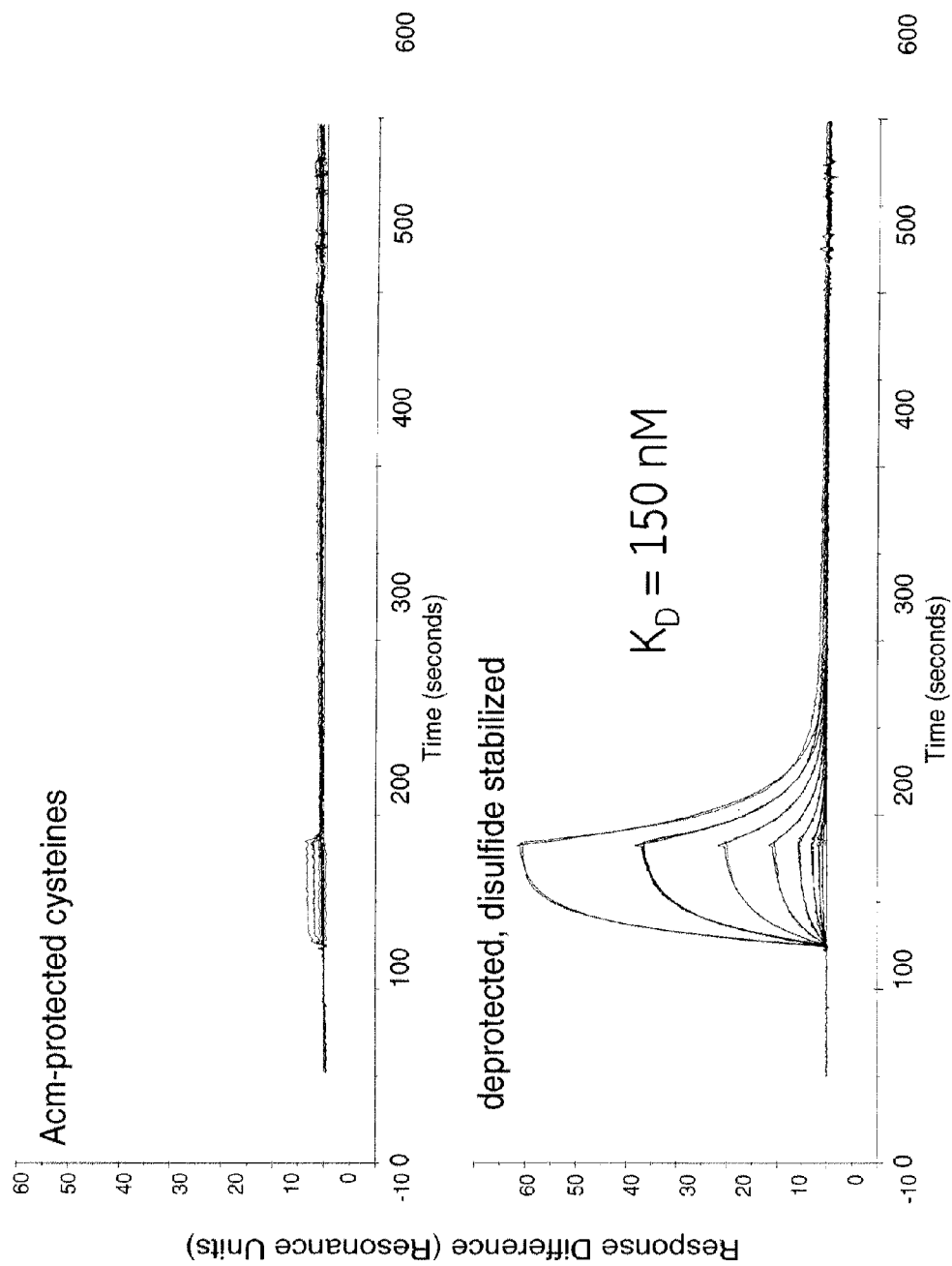

FIG. 5 shows the binding kinetics analysis of anti-Her2 two helix peptide (SEQ. ID. NO.:8), in which binding was measured with a range of concentrations of each peptide between 0-40 nM. The resulting curves were fit using BiaEval software to determine an estimated $K_D$. Curve fitting was not practical for the control peptide, as binding was minimal. Response difference on the X-axis refers to the difference between a Her2-immobilized flow-cell and a control flow-cell.

Figure 6:
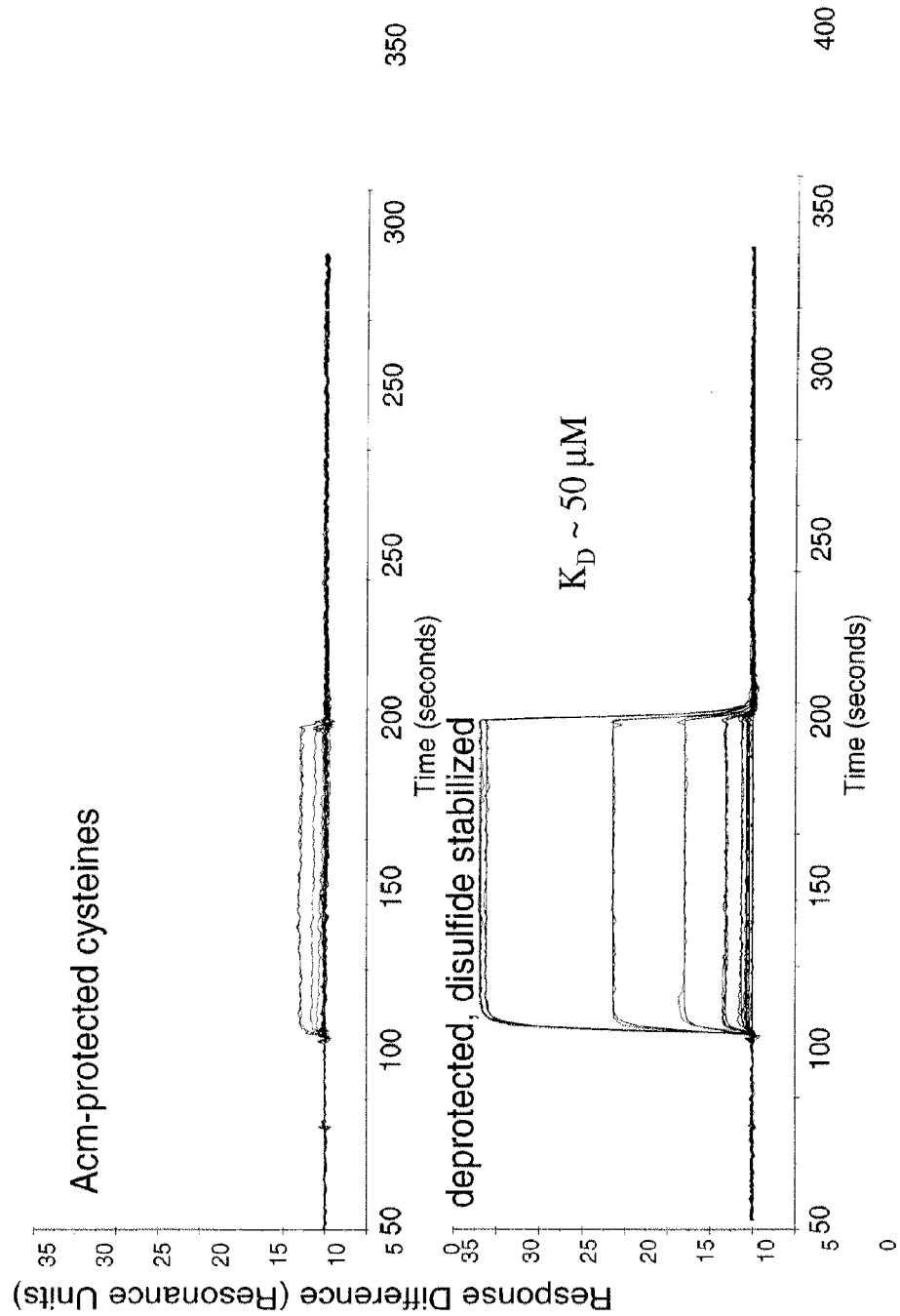

FIG. 6 shows binding kinetics analysis of anti-IgG two helix peptide (SEQ. ID. NO.:7), in which binding was measured with a range of concentrations of each peptide between 0-1 uM. An anti-IgG two alpha-helix peptide was made in the same manner as the anti-Her2 peptide. The resulting curves were fit using BiaEval software to determine an estimated $K_D$. Curve fitting was not practical for the control peptide, as binding was minimal. Response difference on the X-axis refers to the difference between a Her2-immobilized flow-cell and a control flow-cell.

Figure 7A:
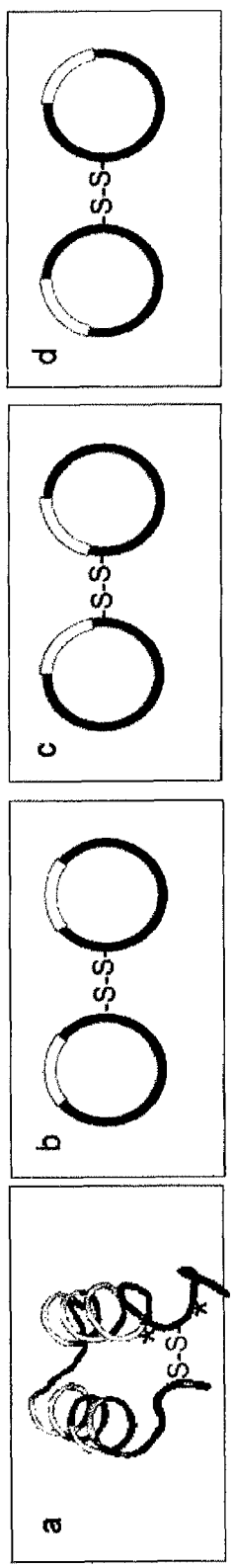

FIG. 7A depicts three potential arrangements of engineered cysteines and the effect on binding to target. Panel a shows the predicted structure of the stabilized two-alpha helix peptide backbone. An example of two potential alternative sites for engineering cysteines are shown with asterisks (*) Panel b shows an arbitrary orientation of the binding residues on the alpha helices. While Panels c and d show examples of how the orientation of the binding residues may change with respect to each other with alternative sites for engineered cysteine residues. These positional changes for a stabilizing disulfide bond will alter the affinity of the peptide for its binding partner, allowing affinity modulation and optimization.

Figure 7B:

FIG. 7B shows the sequence of the anti Her2 two-alpha helix peptide, showing three potential sites for disulfide bond engineering described in FIG. 7, Panel A (SEQ. ID. NO.:8, SEQ. ID. NO.:9 and SEQ. ID. NO.:10).

Figure 7C:
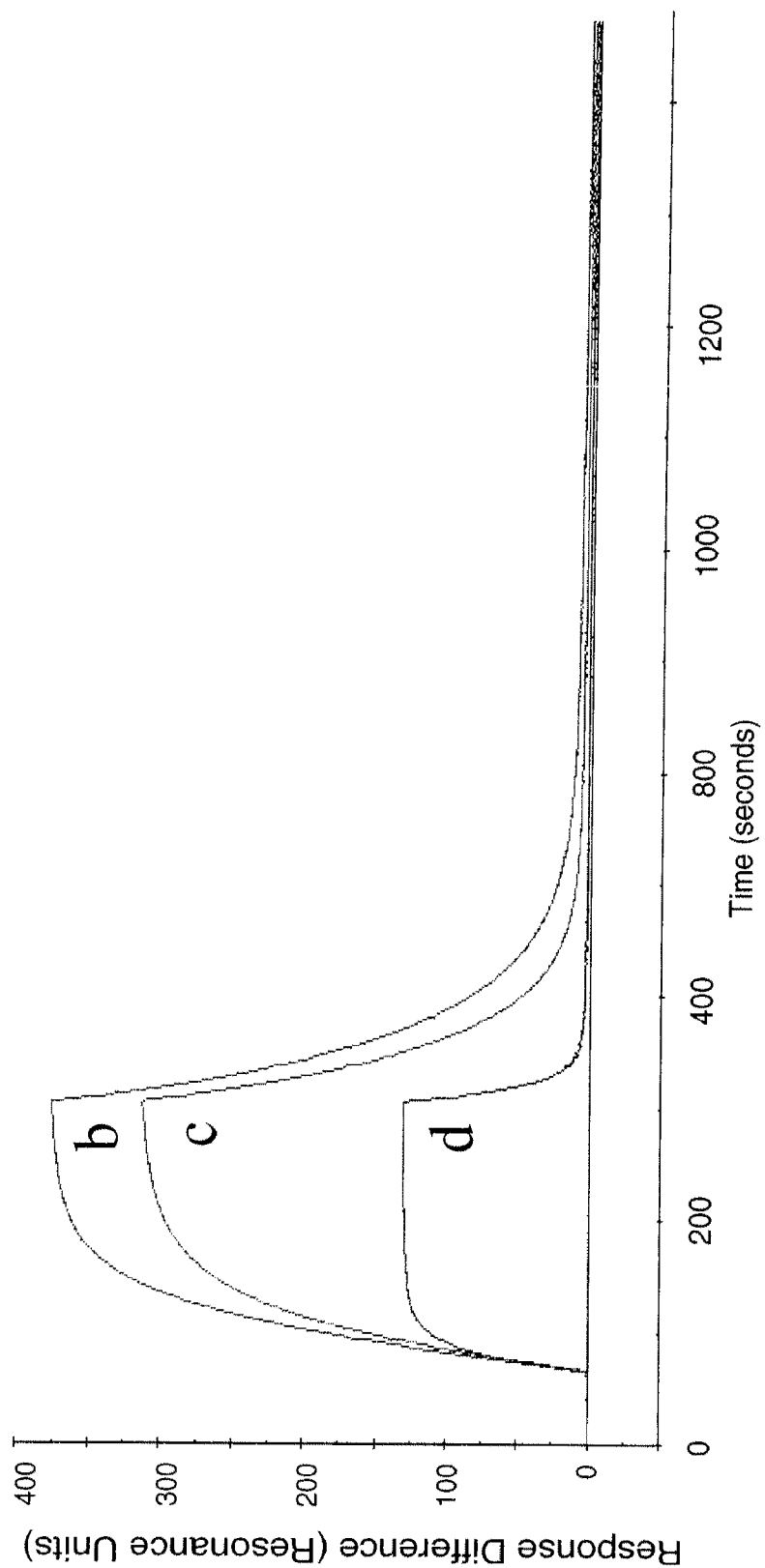

FIG. 7C shows the relative binding analysis of these three peptides to Her2 shows that altering the site of disulfide bond formation results in a corresponding change in affinity for the target.

DETAILED DESCRIPTION

The following detailed description is exemplary and not intended to limit the invention of the application and uses of the invention. Furthermore, there is no intention to be limited by any theory presented in the preceding background of the invention of the following detailed description. To more clearly and concisely describe and point out the subject matter of the claimed invention, the following definitions are provided for specific terms that are used in the following description and the claims appended hereto.

Unless otherwise indicated, the word "a" refers to one or more than one of the word modified by the article "a."

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

"Aliphatic Amino Acid" refers to a hydrophobic amino acid having an aliphatic hydrocarbon side chain. Genetically encoded aliphatic amino acids include Ala (A), Val (V), Leu (L), and Ile (I).

"Amino acid analogs" refer to compounds that have the same basic chemical structure as a naturally occurring amino acid (i.e., a carbon that is bound to a hydrogen, a carboxyl group, an amino group) including a non-conventional R group, (e.g., homoserine, norleucine, methionine sulfoxide, or methionine methyl sulfonium). Such analogs have modified R groups (e.g., norleucine) or modified peptide backbones, but retain the same basic chemical structure as a naturally occurring amino acid.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, γ-carboxyglutamate, O-phosphoserine, phosphothreonine, and phosphotyrosine. Categories of amino acids herein defined are not mutually exclusive. Thus, amino acids having side chains exhibiting two or more physical-chemical properties can be included in multiple categories. For example, amino acid side chains having aromatic moieties that are further substituted with polar substituents, such as Tyr (Y), may exhibit both aromatic hydrophobic properties and polar or hydrophilic properties, and can therefore be included in both the aromatic and polar categories. The appropriate categorization of any amino acid will be apparent to those of skill in the art, in light of the detailed disclosure provided herein.

"Aromatic Amino Acid" refers to a hydrophobic amino acid with a side chain having at least one aromatic or heteroaromatic ring. The aromatic or heteroaromatic ring may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR and the like where each R is independently (C$_1$-C$_6$)alkyl, substituted (C$_1$-C$_6$)alkyl, (C$_1$-C$_6$)alkenyl, substituted (C$_1$-C$_6$)alkenyl, (C$_1$-C$_6$)alkynyl, substituted (C$_1$-C$_6$)alkynyl, (C$_5$-C$_{20}$)aryl, substituted (C$_5$-C$_{20}$)aryl, (C$_6$-C$_{26}$)alkaryl, substituted (C$_6$-C$_{26}$)alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe (F), Tyr (Y), and Trp (W).

"Basic Amino Acid" refers to a hydrophilic amino acid having a side chain pK value of greater than 7. Basic amino acids typically have positively charged side chains at physiological pH due to association with hydronium ion. Genetically encoded basic amino acids include H is (H), Arg (R), and Lys (K).

As used herein, the term "binding" refers to the ability of a two helix binder to preferentially bind to target with an affinity that is at least two-fold greater than its affinity for binding to a non-specific target (e.g., BSA or casein) other than the predetermined target or a closely-related target. The two helix binders provided herein bind their respective targets with an affinity with a KD value less than about $5\times10^5$ M$^{-1}$, more preferably less than about $2\times10^7$ M$^{-1}$, and most preferably less than about $1\times10^8$ M$^{-1}$. Similarly, "specific binding" refers to the property of a binder to bind to a predetermined antigen with an affinity with a KD value less than about $2\times10^7$ M$^{-1}$.

The terms "binding interface residue" and "binding interface residues" refer to those residues of the two helix binder polypeptide involved in target binding, which are exemplified in the representative 39-residue polypeptide shown in Table 1.

The term "binding target" refers to any agent that may be bound by a two helix binder. A binding target may include one or more of peptides, proteins (e.g., antibodies), nucleic acids (e.g., polynucleotides, DNA, RNA, or aptamers); polysaccharides (e.g., lectins or sugars), lipids, enzymes, enzyme substrates, ligands, receptors, antigens, or haptens. The target may include a discrete chemical moiety or a three-dimensional structural component (e.g., 3D structures that arises from peptide folding).

A "cloning vector" is a nucleic acid molecule, for example, a plasmid, cosmid, or bacteriophage that has the capability of replicating autonomously in a host cell. Cloning vectors typically contain (i) one or a small number of restriction endonuclease recognition sites at which foreign DNA sequences can be inserted in a predictable fashion without loss of an essential biological function of the vector, and (ii) a marker gene that is suitable for use in the identification and selection of cells transformed or transfected with the cloning vector. Marker genes include genes that provide tetracycline resistance or ampicillin resistance, for example. The term vector refers to any autonomously replicating or integrating agent, including but not limited to plasmids, cosmids, and viruses (including phage), comprising a nucleic acid molecule to which one or more additional nucleic acid molecules may be added.

The terms "conservative variant" and "conservative variants" used herein apply to both amino acid and nucleic acid sequences. With respect to particular nucleic acid sequences, conservative variants refer to those nucleic acids that encode identical or similar amino acid sequences and include degenerate sequence s. For example, the codons GCA, GCC, GCG, and GCU all encode alanine. Thus, at every amino acid position where an alanine is specified, any of these codons may be used interchangeably in constructing a corresponding nucleotide sequence. The resulting nucleic acid variants are conservatively modified variants, since they encode the same protein (assuming that is the only alteration in the sequence). One skilled in the art recognizes that each codon in a nucleic acid, except for AUG (sole codon for methionine) and UGG (tryptophan), may be modified conservatively to yield a functionally identical peptide or protein molecule.

As to amino acid sequence substitutions, deletions, or additions to a polypeptide or protein sequence that alter, add or delete a single amino acid or a small number typically less than about 10% of amino acids is a "conservative variant" where the alteration results in the substitution of an amino acid with a chemically similar amino acid. Conservative substitutions are well known in the art and include, for example, the changes of: alanine to serine; arginine to lysine; asparigine to glutamine or histidine; aspartate to glutamate; cysteine to serine; glutamine to asparigine; glutamate to aspartate; glycine to proline; histidine to asparigine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

The term "poor helix formers" refers to amino acid residues with a propensity to disrupt the structure of α helices when contained at internal positions within the helix. Ala (A), Glu (E), Lys (K), Leu (L), Met (M), and Arg (R) are good alpha-helix formers, while Pro (P), Gly (G), Tyr (Y), and Ser (S) are poor alpha-helix formers. However, all poor alpha helix formers have been successfully substituted into the binding interface of the Z domain scaffold while still retaining binding affinity for a target. Of these residues, Pro (P) is not preferred for substitution of residues within a helix because of its rigid structure. Furthermore, D-amino acids may disrupt helical structure when contained in a L-peptide and, likewise, L-amino acids disrupt helical structure when contained in a D-peptide. Thus, in some embodiments, the amino acids comprising the two helix binder polypeptides substantially consist of amino acids of a single isomeric orientation (i.e., mostly D-peptides or mostly L-peptides).

"Hydrophilic Amino Acid" refers to an amino acid exhibiting a hydrophobicity of less than zero according to the normalized consensus of the Eisenberg hydrophobicity scale. Genetically encoded hydrophilic amino acids include Thr (T), Ser (S), H is (H), Glu (E), Asn (N), Gln (O), Asp (D), Lys (K), and Arg (R).

"Hydrophobic Amino Acid" refers to an amino acid exhibiting a hydrophobicity of greater than zero according to the normalized consensus hydrophobicity Eisenberg scale. Genetically encoded hydrophobic amino acids include Pro (P), Ile (I), Phe (F), Val (V), Leu (L), Trp (W), Met (M), Ala (A), Gly (G) and Tyr (Y).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G), and Ala (A).

"Polar Amino Acid" refers to a hydrophilic amino acid having a side chain that is uncharged at physiological pH, but which has at least one bond in which the pair of electrons shared in common by two atoms is held more closely by one of the atoms. Polar amino acids include Asn (N), Gln (Q), Ser (S), and Thr (T).

The term "scaffold" with reference to helical binders generally refers to those residues of the two helix binder polypeptide that provides the three-dimensional structure to adequately position the binding interface residues of the polypeptide such that binding to a target is enabled. Specifically, residues 2 though 14 of the first α helix and residues 20 through 32 of SEQ ID NO.:2 of the second α helix contribute to the helical segment of the two helix binder scaffold and residues 15 through 19 contribute to a loop segment of the two helix binder scaffold thereby effecting the relative orientation of the helices and binding to target of SEQ ID NO.:2. Residues 1 through 5 and 37 through 39 of SEQ ID NO.:4 contribute to non-helical termini, which may also contribute to proper orientation of the helices.

As used herein, the term "signal generator" refers to a molecule capable of providing a detectable signal using one or more detection techniques including, for example, spectrometry, calorimetry, spectroscopy, or visual inspection.

Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Embodiments

In general, the two helix binders provided herein may be used to perform the functions that other binders (e.g., antibodies) are used to perform. Thus, the two helix binders may be used, for example, as capture agents (e.g., an affinity selection agent) or as detection agents (e.g., an ELISA agent). When used as detection agents the two helix binders may be modified to generate a signal by the addition of a label (e.g., a fluorophore or a radioisotope). When used as capture agents, the two helix binders may be modified to include a tag (e.g., a his tag) that enhances the ability to the two helix binder to bind to an affinity column.

The two helix binding polypeptides may be generated using standard solid phase synthesis techniques, for example, as described below in Example 1. Alternatively, the polypeptides may be generated using recombinant techniques. In embodiments where the polypeptides are generated using recombinant techniques, the DNA encoding the polypeptides or conservative variants thereof may be isolated. The DNA encoding the polypeptides or conservative variants thereof may be inserted into a cloning vector, introduced into a host cell (e.g., a eukaryotic cell, a plant cell, or a prokaryotic cell), and expressed using any art recognized expression system.

Whether the polypeptide is generated using peptide synthesis techniques or recombinant techniques, the polypeptides generated may be substantially comprised of a single chiral form of amino acid residues. Thus, polypeptides of the invention may be substantially comprised either L-amino acids or D-amino acids; although a combination of L-amino acids and D-amino acids may also be employed.

As the polypeptides provided herein are derived from the Z-domain of protein A (SEQ. ID. NO.:1.), residues on the binding interface may be non-conservatively substituted or conservatively substituted while preserving binding activity. In some embodiments, the substituted residues may be any of the 20 naturally occurring amino acids or any of analog thereof.

The two helix binders provided herein consist essentially of polypeptides approximately 39 residues in length. The length of the polypeptides may be about 28 residues to about 41 residues or about 30 to about 35 amino acids.

Additional sequence may be added to the termini to impart selected functionality. Thus, additional sequences may be appended to one or both termini to facilitate purification or isolation of a two helix binder, alone or coupled to a binding target (e.g., by appending a his tag to the polypeptide). A signal generator may be incorporated into the polypeptide at terminal position or at an internal position. Suitable examples of signal generators may include a chromophore, a fluorophore, a Raman-active tag, a radioactive label, an enzyme, an enzyme substrate, or combinations thereof. Suitable examples of a detectable signal may include an optical signal, and electrical signal, or a radioactive signal. In some instances the signal generator and the binder are present in a single entity (e.g., a target binding protein with a fluorescent label or radiolabel). And, in other embodiments the binder and the signal generator are discrete entities (e.g., target receptor protein and antibody against the that particular receptor protein) that associate with each other following introduction to the sample.

A linker moiety may be appended to the polypeptide to facilitate linkage to a separate chemical entity (e.g., a tag or a label). The two helix binder polypeptides disclosed herein may be further modified to enhance pharmokinetics (e.g., by appending polyglycans to modulate blood circulation half life).

The polypeptides provided herein may be comprised of naturally occurring amino acids and analogues of naturally occurring amino acids. In some embodiments, the polypeptides may contain a single enantiomer of an amino acid residue. In alternative embodiments, the polypeptides may contain a combination of D- and L-forms of amino acids.

Methods available for substitution of amino acids include mutagenesis of the cDNA encoding the described polypeptide by a number of methods known to those skilled in the art, including random mutagenesis, site-directed mutagenesis, and mutagenesis using error prone PCR. A preferred method to introduce random substitutions into the binding interface positions is the use of DNA containing degenerate primers (e.g., NNK) at the codons of desired substitution.

Substitutions of residues in either the polypeptide provided herein with prolines or cysteines are generally disfavored. However, prolines and cysteines may occur in the polypeptides of the invention under certain conditions.

Proline, as a poor helix former is generally disfavored. However, Z-domain polypeptides containing prolines are know to be capable of binding target. Consequently, proline substitutions in the scaffold portions of the polypeptide are not absolutely prohibited, but should be limited to less than about 20% of the total scaffold residues. Similarly, proline substitutions in the binding interface are also disfavored but are permitted.

Cysteine residues may form intermolecular or intramolecular disulfide bridges with other cysteine residue. Therefore, other than the cysteine residues and their positions in the two helix binders disclosed herein, additional cysteines are not preferred, especially if more than one, as unwanted disulfide formation and structural changes may occur. An exception to this scenario may be when an additional thiol moiety via a cysteine is desired to form a dimer of the two helix binder by an intermolecular disulfide formation.

Although cysteine substitutions within the binding interface are generally disfavored, in some embodiments, residues in the binding interface may be substituted with cysteine residues under certain conditions. Thus, if a non-cysteine residues is replaced with cysteine residues, the substitution is preferably replaced in two positions such that the thiol reactive group in the pair of substituted cysteine residues that are positioned to permit formation of a disulfide bridge to enhance stability of a helix. The substitution of cysteine in pairs that are capable of forming disulfide bridges further avoids disfavored constructs in which an unpaired reactive thiol group is present in the polypeptide.

Similarly, although a proline substitution within the binding interface is generally disfavored, in some embodiments, residues in the binding interface may be substituted with proline under certain conditions. Thus, if proline residues are substituted in the polypeptides, the total number of proline substitutions should be limited to less than about 10% of the total number of residues in the polypeptide.

For an amino acid identified for a position in the two helix binder in the polypeptide shown in Table 1 to obtain binding to a target, conservative changes are permitted (e.g., one polar amino acid may potentially be substituted for another polar residue). Non-conservative changes are also permitted in the binding interface, but only if improvement in binding occurs.

In general, a single amino acid should not comprise more than about 60% of the total number of interface amino acids. In embodiments where the target comprises multiple repeat structures (e.g., collagen) more than 60% of a singe amino acid may be allowed in the binding interface.

Although, the scaffold portions of the polypeptides are preferred to be unchanged so as to preserve the two helix binding conformation, conservative and non-conservative mutations in scaffold residues that do not result in a loss of binding are permitted wherein the total non-conservative substitutions being restricted to fewer than about 20% of the total number of helical portions of the scaffold. In general, substitutions of proline residues are disfavored, but are not strictly prohibited. An exemplary 39 residue two helix polypeptide is provided in Table 1 below, in which generally favored and disfavored substitutions are indicated.

TABLE 1

| Amino Acid | Function | Favored Substitutions | Disfavored Substitutions |
|---|---|---|---|
| V | Scaffold, terminus | Cys | None |
| $X_1$ | Scaffold, terminus | Cys | None |
| N | Scaffold, terminus | Cys | None |
| K | Scaffold, terminus | Cys | None |
| F | Scaffold, terminus | Cys, Conserved | Non-conserved |
| N | Scaffold, helix | Cys, Conserved | Non-conserved |
| K | Scaffold, helix | Cys, Conserved | Non-conserved |
| E | Scaffold, helix | Cys, Conserved | Non-conserved |
| $X_2$ | Binding Interface | ADEFGHIKLMNPQRSTVW | Cys, Pro |

TABLE 1-continued

| Amino Acid | Function | Favored Substitutions | Disfavored Substitutions |
|---|---|---|---|
| $X_2$ | Binding Interface | ADEFGHIKLMNPQRSTVW | Cys, Pro |
| $X_2$ | Binding Interface | ADEFGHIKLMNPQRSTVW | Cys, Pro |
| A | Scaffold, helix | Conserved | Non-conserved |
| $X_2$ | Binding Interface | ADEFGHIKLMNPQRSTVW | Cys, Pro |
| $X_2$ | Binding Interface | ADEFGHIKLMNPQRSTVW | Cys, Pro |
| E | Scaffold, helix | Conserved | Non-conserved |
| I | Scaffold, helix | Conserved | Non-conserved |
| $X_2$ | Binding Interface | ADEFGHIKLMNPQRSTVW | Cys, Pro |
| $X_2$ | Binding Interface | ADEFGHIKLMNPQRSTVW | Cys, Pro |
| L | Scaffold, loop | Conserved | Non-conserved |
| P | Scaffold, loop | None | Non-conserved |
| N | Scaffold, loop | Conserved | Non-conserved |
| L | Scaffold, loop | Conserved | Non-conserved |
| N | Scaffold, loop | Conserved | Non-conserved |
| $X_2$ | Binding Interface | ADEFGHIKLMNPQRSTVW | Cys, Pro |
| $X_2$ | Binding Interface | ADEFGHIKLMNPQRSTVW | Cys, Pro |
| Q | Scaffold, helix | Conserved | Non-conserved |
| $X_2$ | Binding Interface | ADEFGHIKLMNPQRSTVW | Cys, Pro |
| $X_2$ | Binding Interface | ADEFGHIKLMNPQRSTVW | Cys, Pro |
| A | Scaffold, helix | Conserved | Non-conserved |
| F | Scaffold, helix | Conserved | Non-conserved |
| I | Scaffold, helix | Conserved | Non-conserved |
| $X_2$ | Binding Interface | ADEFGHIKLMNPQRSTVW | Cys, Pro |
| S | Scaffold, helix | Conserved | Non-conserved |
| L | Scaffold, helix | Conserved | Non-conserved |
| $X_2$ | Binding Interface | ADEFGHIKLMNPQRSTVW | Cys, Pro |
| D | Scaffold, helix | Cys, Conserved | Non-conserved |
| D | Scaffold, terminus | Cys, Conserved | Non-conserved |
| P | Scaffold, terminus | Cys | None |
| S | Scaffold, terminus | Cys | None |

In general, the two helix binders provided herein demonstrate a binding affinity for the target in the range of about 50 µM to about 200 nM. The anti-IgG two helix binder described below in the Examples (SEQ ID NO.:7) has demonstrated an affinity of about 50 µM for its target, IgG. The anti-HER2 two helix binder described in the Examples below (SEQ ID NO.:8) has demonstrated an affinity of about 150 nM for its target, HER2.

Table 2 below provides sequences referred to herein.

TABLE 2

SEQ ID NO.:1 shows the sequence for the protein A Z domain:
VDNKFNKEQQNAFYEILHLPNLNEEQRNAFIQSLKDDPSQSANLLAEAKKLNDAQAPK
SEQ ID NO.:2 shows a 35-residue protein A sequence in which the scaffold residues are shown as X2, which may be any amino acid:
FNKEX$_2$X$_2$X$_2$AX$_2$X$_2$EIX$_2$X$_2$LPNLNX$_2$X$_2$QX$_2$X$_2$AFIX$_2$SLX$_2$DDPS.
SEQ ID NO.:3 shows a representative sequence that may be added to N-terminus of a two helix polypeptide, wherein X$_1$ may be D or E: VX$_1$NK
SEQ ID NO.:4 shows a representative sequence in which SEQ ID NO:2 and SEQ ID NO.3 are combined, wherein X$_1$ may be D or E:
VX$_1$NKFNKEX$_2$X$_2$X$_2$AX$_2$X$_2$EIX$_2$X$_2$LPNLNX$_2$X$_2$QX$_2$X$_2$AFIX$_2$SLX$_2$DDPS
SEQ ID NO.:5 shows a representative anti-IgG two helix binder, wherein X$_1$ may be D or E:
VX$_1$NKFNKEQQNAFYEILHLPNLNEEQRNAFIQSLKDDPS
SEQ ID NO.:6 shows a representative anti-Her2 two helix binder; wherein X$_1$ may be D or E:
VX$_1$NKFNKEMRNAYWEIALLPNLNNQQKRAFIRSLYDDPS
SEQ ID NO.:7 shows a representative anti-IgG two helix binder with preferred substitutions with cysteine:
VENKCNKEQQNAFYEILHLPNLNEEQRNAFIQSLKDDPC
SEQ ID NO.:8 shows a representative anti-Her2 two helix binder with preferred substitutions with cysteine:
VENKCNKEMRNAYWEIALLPNLNNQQKRAFIRSLYDDPC
SEQ ID NO.:9 shows a representative anti-Her2 two helix binder with alternative substitutions with cysteine:
VENKFCKEMRNAYWEIALLPNLNNQQKRAFIRSLYDDPC
SEQ ID NO.:10 shows a representative anti-Her2 two helix binder with alternative substitutions with cysteine:
VENCFNKEMRNAYWEIALLPNLNNQQKRAFIRSLYDDPC

EXAMPLES

Practice of the invention will be still more fully understood from the following examples, which are presented herein for illustration only and should not be construed as limiting the invention in any way.

Example 1

Peptide Synthesis & Purification

Selection and determination of two helix polypeptides with binding interface amino acids that bind to a particular target may be accomplished using art recognized display and selection methods such as phage display, ribosomal display, mRNA display yeast surface display, or bacterial surface display techniques. Alternatively, the two helix polypeptides may be designed and synthesized using art recognized techniques as detailed below.

Materials: All N-Fmoc (Fluorenylmethoxycarbonyl)-protected amino acids were purchased from Advanced Chemtech (Louisville, Ky.) except for Fmoc-Cysteine-Acetamidomethyl(Acm)-OH, which was from Novabiochem (San Diego, Calif.). DMF was from Fisher Scientific (Fair Lawn, N.J.). 20% piperidine in DMF and N-methylmorpholine (NMM) in DMF were from Protein Technologies Inc. (Tucson, Ariz.). Trifluoroacetic acid (TFA) and O-(7-azabenzotriazol-1-yl)-N,N,N',N'-trimethyluronium hexafluorophosphate (HATU) was from Advanced Chemtech. Pyridine, acetic anhydride, and anhydrous ether were obtained from J.T.Baker (Phillipsburg, N.J.). Triisopropylsilane (TIS) was purchased from Aldrich Chemical Company (Milwaukee, Wis.). HPLC grade acetonitrile ($CH_3CN$) and Millipore 18 m$\Omega$ water were used for peptide purifications.

Peptides were synthesized using standard solid phase techniques with N-Fmoc-protected amino acids using 0.2 mmol/g substitution 2,4-dimethoxybenzhydrylamine resin (Rink Resin LS, Advanced Chemtech) on a 50 µM scale. The peptides were synthesized using a Rainin/Protein Technology, Inc. Symphony solid phase peptide synthesizer (Woburn, Mass.).

Prior to any chemistry, the resin was swelled for one hour in Methylene Chloride, subsequently the solvent was exchanged by washing with dimethylformamide (DMF). Each coupling reaction was carried out at room temperature in DMF with five equivalents of amino acid. Reaction times were typically 30 minutes; however residues that were expected to be difficult to couple (for example, bulky trityl-protected residues in the latter half of synthesis were either coupled for 45 minutes or double coupled (20 minutes×2). The coupling reagent used was HATU with NMM as the base. For each step the coupling agent was delivered at a scale of five equivalents relative to the estimated resin capacity, and reaction carried out in 5.0 ml of 0.05 M amino acid reagent, 0.05 M HATU, 0.2 M NMM solution in DMF.

The reactions did not perturb the side-chains of the amino acids, which were typically protected with acid labile groups if reactive groups were present. Generally, the tyrosine, threonine, serine, and aspartic acid side chains were protected as the corresponding tert-butyl esters. The lysine side chains were t-Butoxycarbonyl (Boc) protected. The glutamine side chain was protected as the N-$\gamma$-trityl derivative, and the arginine side chain was protected as the 2,2,5,7,8-Pentamethyl-chromane-6-sulfonyl derivative. The cysteine amino acid side chain thiol group was protected with Acm.

Following each coupling reaction, the N-terminal Fmoc-protected amine was deprotected by applying 20% piperidine in DMF twice at room temperature for approximately 15 minutes. After the addition of the last residue the resin, still on the peptide synthesizer, was rinsed thoroughly with DMF and methylene chloride before being dried under a stream of nitrogen for 20 minutes.

To cleave the peptides from the resin a cocktail consisting of 10 mL 95% TFA, 2.5% TIS and 2.5% water was used. The resin and cocktail were stirred at room temperature for approximately 4 hours. This cocktail did not remove the Acm protecting group on the cysteine thiols. The resin beads were removed by filtering through a polyethylene disc with 30 um pore size. The peptide was precipitated with 40 ml of ice-cold ether and centrifuged at 3000 r.c.f. until the precipitate formed a pellet at the bottom of the centrifuge tube. The ether was decanted, and the pellet was resuspended in cold ether and centrifuged again; this process was repeated two times. Between 10 ml and 40 ml of water was added to the decanted pellet to solubilize the peptide and the resulting solution was lyophilized.

Peptides were purified by reverse phase preparative HPLC with a C4-silica column (Vydac, Hesperia, Calif.). The peptide chromatograms can be monitored at 220 nm, which corresponds to the absorption of the amide chromophore. A solvent system including $CH_3CN$/TFA (acetonitrile/Trifluoroacetic acid; 100:0.05) and $H_2O$/TFA (water/Trifluoroacetic acid; 100:0.05) eluents at flow rates of 25 ml/min preparative runs. Dissolved crude peptides in Millipore water can be injected at a scale of 1.5 mg and 5-10 mg peptide for semi-preparative or preparative, respectively. The chromatogram shape was analyzed to ensure good resolution and peak shape. Gradient conditions for all peptides were typically 0.5% of $CH_3CN$/TFA (100:0.01) per minute. Target peptide identity was confirmed by matrix-assisted laser desorption time-of-flight mass spectroscopy (MALDI) or electrospray ionization mass spectrometry (ESI).

After initial purification, the Acm-protecting group was removed from the peptide using a one step deprotection/oxidization reaction in the presence of iodine. This step was carried out using concentrations favorable to intramolecular disulfide formation (0.1 mg/ml). Peptide was dissolve in 1:1 water:Acetic acid at ~1 mg/ml or less. Nine volumes of 1 M HCl were then added followed by 10 equivalents $I_2$/Acm of a 0.1 M $I_2$ solution. This solution was vigorously stirred for 30 minutes at room temperature and the reaction was quenched by the dropwise addition of 1M sodium thiosulfate until the solution became clear. This resulting product was then purified using the same reverse phase HPLC gradient as the initial purification. The desired fractions were frozen immediately and lyophilized. Target peptide identity was confirmed by MALDI or ESI.

Example 2

Target Binding Analysis

Binding interactions between the binder and the Her2/neu antigen (Her2 was measured in vitro using surface plasmon resonance (SPR) detection on a BIAcore™ 3000 instrument (Piscataway, N.J.). The extracellular domain of the Her2/neu antigen was obtained as a conjugate with the Fc region of human IgG (Fc-Her2) from R&D Systems ( ) and covalently attached to a CM-5 dextran-functionalized sensor chip (BIAcore™) pre-equilibrated with HBS-EP buffer (0.01M HEPES pH 7.4, 0.15M NaCl, 3 mM EDTA, 0.005% v/v surfactant P20) at 10 uL/min and subsequently activated with 1-ethyl-3-[3-dimethylaminopropyl]carbodiimide hydrochloride (EDC) and N-hydroxysuccinimide (NHS). The Fc-Her2 (5

μg/ml) in 10 mM sodium acetate (pH 5.5) was injected onto the activated sensor chip until the desired immobilization level was achieved (2 min). Residual activated groups on the sensor chip were blocked by injection of ethanolamine (1 M, pH 8.5). Any non-covalently bound conjugate was removed by repeated (5×) washing with 2.5 M NaCl$_2$, 50 mM NaOH.

A second flow cell on the same sensor chip was treated identically, except with no Fc-Her2 immobilization, to serve as a control surface for refractive index changes and non-specific binding interactions with the sensor chip. Prior to the kinetic study, binding of the target analyte was tested on both surfaces and a surface stability experiment was performed to ensure adequate removal of the bound analyte and regeneration of the sensor chip following treatment with 2.5 M NaCl$_2$, 50 mM NaOH. SPR sensorgrams were analyzed using the BiaEval (BIAcore) software. The robustness of the kinetic model was determined by evaluation of the residuals and standard error for each of the calculated kinetic parameters, the "goodness of the fit" ($\chi 2 < 10$), and a direct comparison of the modeled sensorgrams to the experimental data.

The binding interactions between the generated peptide and Fc-Her2 conjugate were measured using SPR (BIAcore). To minimize mass transport limitations, a surface density of ~3000 RUs Fc-Her2 was used, resulting in a maximal binding response ~100 RU with ~100 nM of the synthesized peptide. SPR measurements were collected at eight analyte concentrations (0-100 nM peptide) and the resulting sensorgrams were fitted to a 1:1 Langmuir binding model.

For analysis of the IgG binding peptide, the same protocol was followed as above except that human IgG was immobilized by injecting 20 μg/ml in 10 mM sodium acetate (pH 5.0) onto the activated sensor chip until the desired immobilization level was achieved (2 minutes).

EQUIVALENTS

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

The invention claimed is:

1. An isolated polypeptide comprising a two helix segment derived from the Z domain of protein A that is capable of binding the Fc region of IgG and wherein the isolated polypeptide comprises a disulfide bond between two members of a thiol-containing pair of residues, wherein both members of the disulfide pair are positioned outside of the binding interface of the polypeptide and wherein the first amino acid of the binding interface is positioned eleven amino acids in an N-terminal direction relative to a conserved proline, wherein the conserved proline is an internal residue within the isolated polypeptide and wherein the isolated polypeptide comprises more than eleven amino acids in the N-terminal direction relative to the conserved proline, wherein the isolated polypeptide comprises a variant of SEQ ID NO. 4 modified by a substitution that comprises substituting two amino acids with the thiol-containing residues and wherein Xaa is any naturally occurring amino acid except cysteine.

2. The isolated polypeptide of claim 1, wherein $X_1$ of SEQ ID No. 4 is Glu or Asp.

3. The isolated polypeptide of claim 1, wherein the first member of the disulfide pair is located at one of residue 1 through residue 8 and the second member of the disulfide pair is located at one of residue 36 through residue 39 of SEQ ID NO. 4.

4. The isolated polypeptide of claim 1, wherein the first member of the disulfide pair is located at one of residue 1 through residue 8 and the second member of the disulfide pair is located at appended residue 40 of SEQ ID NO. 4.

5. The isolated polypeptide of claim 1, wherein the first member of the disulfide pair is located at one of residue 4 through residue 6 and the second member of the disulfide pair is located at residue 39 of SEQ ID NO. 4.

6. The isolated polypeptide of claim 1, wherein the first member of the disulfide pair is located at residue 5 and the second member of the disulfide pair is located at residue 39 or appended residue 40 of SEQ ID NO. 4.

7. The isolated polypeptide of claim 1, the sequence of which consists of SEQ ID NO. 7.

8. The isolated polypeptide of claim 1, the sequence of which consists of SEQ ID NO. 8.

9. The isolated polypeptide of claim 1, the sequence of which consists of SEQ ID NO. 9.

10. The isolated polypeptide of claim 1, the sequence of which consists of SEQ ID NO. 10.

11. The isolated polypeptide of claim 1, further comprising a signal generator attached to the polypeptide.

* * * * *

```
                       SEQUENCE LISTING

<160> NUMBER OF SEQ ID NOS: 10

<210> SEQ ID NO 1
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 2
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (13)..(14)
<223> OTHER INFORMATION: Any amino acid
<220> FEATURE:
<221> NAME/KEY: MOD_RES
<222> LOCATION: (20)..(21)
<223> OTHER INFORMATION: Any amino acid
```

-continued

```
<220> FEATURE:
<221> NAME/KEY: MOD_RES
<222> LOCATION: (23)..(24)
<223> OTHER INFORMATION: Any amino acid
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (31)..(31)
<223> OTHER INFORMATION: Any amino acid

<400> SEQUENCE: 2

Phe Asn Lys Glu Xaa Xaa Xaa Ala Xaa Xaa Glu Ile Xaa Xaa Leu Pro
1               5                   10                  15

Asn Leu Asn Xaa Xaa Gln Xaa Xaa Ala Phe Ile Xaa Ser Leu Xaa Asp
            20                  25                  30

Asp Pro Ser
        35

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asp or Glu

<400> SEQUENCE: 3

Val Xaa Asn Lys
1

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Asp or Glu
<220> FEATURE:
<221> NAME/KEY: MOD_RES
<222> LOCATION: (9)..(11)
<223> OTHER INFORMATION: Any amino acid
<220> FEATURE:
<221> NAME/KEY: MOD_RES
<222> LOCATION: (13)..(14)
<223> OTHER INFORMATION: Any amino acid
<220> FEATURE:
<221> NAME/KEY: MOD_RES
<222> LOCATION: (17)..(18)
<223> OTHER INFORMATION: Any amino acid
<220> FEATURE:
<221> NAME/KEY: MOD_RES
<222> LOCATION: (24)..(25)
<223> OTHER INFORMATION: Any amino acid
<220> FEATURE:
<221> NAME/KEY: MOD_RES
<222> LOCATION: (27)..(28)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
```

```
<222> LOCATION: (35)..(35)
<223> OTHER INFORMATION: Any amino acid

<400> SEQUENCE: 4

Val Xaa Asn Lys Phe Asn Lys Glu Xaa Xaa Ala Xaa Xaa Glu Ile
1               5                   10                  15

Xaa Xaa Leu Pro Asn Leu Asn Xaa Xaa Gln Xaa Xaa Ala Phe Ile Xaa
            20                  25                  30

Ser Leu Xaa Asp Asp Pro Ser
        35

<210> SEQ ID NO 5
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Asp or Glu

<400> SEQUENCE: 5

Val Xaa Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser
        35

<210> SEQ ID NO 6
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Asp or Glu

<400> SEQUENCE: 6

Val Xaa Asn Lys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Ser
        35

<210> SEQ ID NO 7
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Val Glu Asn Lys Cys Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Cys
```

-continued

```
<210> SEQ ID NO 8
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Val Glu Asn Lys Cys Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Cys
        35

<210> SEQ ID NO 9
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Val Glu Asn Lys Phe Cys Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Cys
        35

<210> SEQ ID NO 10
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Val Glu Asn Cys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Cys
        35
```